(12) United States Patent
Tung et al.

(10) Patent No.: US 8,426,655 B2
(45) Date of Patent: Apr. 23, 2013

(54) PROCESS FOR THE MANUFACTURE OF HEXAFLUORO-2-BUTENE

(75) Inventors: Hsueh Sung Tung, Getzville, NY (US); Haiyou Wang, Amherst, NY (US)

(73) Assignee: Honeywell International Inc., Morristown, NJ (US)

( * ) Notice: Subject to any disclaimer, the term of this patent is extended or adjusted under 35 U.S.C. 154(b) by 139 days.

(21) Appl. No.: 13/045,893

(22) Filed: Mar. 11, 2011

(65) Prior Publication Data

US 2011/0237843 A1   Sep. 29, 2011

Related U.S. Application Data

(60) Provisional application No. 61/317,868, filed on Mar. 26, 2010.

(51) Int. Cl.
| | |
|---|---|
| *C07C 17/00* | (2006.01) |
| *C07C 21/18* | (2006.01) |
| *C07C 23/00* | (2006.01) |
| *C07C 25/00* | (2006.01) |
| *C07C 21/00* | (2006.01) |
| *C07C 19/08* | (2006.01) |

(52) U.S. Cl.
USPC .......... 570/151; 570/153; 570/123; 570/164; 570/171

(58) Field of Classification Search .................. None
See application file for complete search history.

(56) References Cited

U.S. PATENT DOCUMENTS

| | | |
|---|---|---|
| 5,210,340 A | 5/1993 | Bielefeldt et al. |
| 5,516,951 A | 5/1996 | Aoyama |
| 5,608,128 A | 3/1997 | Nakada et al. |
| 2003/0002057 A1 | 1/2003 | Kono et al. |
| 2006/0106263 A1 | 5/2006 | Miller et al. |

FOREIGN PATENT DOCUMENTS

WO   2009117458 A2   9/2009

*Primary Examiner* — Sudhakar Katakam
*Assistant Examiner* — Clinton Brooks
(74) *Attorney, Agent, or Firm* — Bruce O. Bradford

(57) ABSTRACT

Hexafluoro-2-butene (HFO-1336) is a low global warming potential blowing agent, refrigerant and solvent. This invention provides methods for making the compound, including the cis-isomer, from the readily available raw materials, carbon tetrachloride and ethylene. The trans-isomer formed in the process can be isomerized into cis-isomer by the use of an isomerization catalyst.

44 Claims, No Drawings

PROCESS FOR THE MANUFACTURE OF HEXAFLUORO-2-BUTENE

CROSS-REFERENCE TO RELATED APPLICATION

This application claims domestic priority from commonly owned, copending, U.S. Provisional Patent Application Ser. No. 61/317,868, filed 26 Mar. 2010, the disclosure of which is hereby incorporated herein by reference.

BACKGROUND OF THE INVENTION

Hexafluoro-2-butene (HFO-1336) is a low global warming potential blowing agent, refrigerant and solvent. This invention provides a method for making the compound, including the cis-isomer, which has the following structure:

SUMMARY OF THE INVENTION

The present invention provides a new and economical process to produce hexafluoro-2-butene (HFO-1336) from readily available raw materials, carbon tetrachloride ($CCl_4$) and ethylene. Without wishing to be bound by theory, it is believed that the hexafluoro-2-butene is produced through several possible intermediates including, $CCl_3CH_2CH_2Cl$, $Cl_3CH=CH_2$, $CCl_3CHClCH_2CCl_3$, and $CF_3CHClCH_2CF_3$. The trans-isomer produced from this technology can be isomerized into cis-isomer over a judiciously selected isomerization catalyst.

One embodiment of the present invention is a process for the manufacture of hexafluoro-2-butene comprising the steps of:

(a) contacting carbon tetrachloride with ethylene in the presence of an effective amount of a metal catalyst complex comprising a metal and an organic ligand under conditions effective to facilitate an addition reaction and to form a product stream comprising 1,1,1,3-tetrachloropropane, (b) dehydrochlorinating the 1,1,1,3-tetrachloropropane formed in step (a) in the absence or presence of a dehydrochlorination catalyst under conditions effective to form a product stream comprising 3,3,3-trichloro-1-propene and/or 1,1,3-trichloro-1-propene, (c) contacting carbon tetrachloride with the 3,3,3-trichloro-1-propene and/or 1,1,3-trichloro-1-propene formed in step (b) in the presence of an effective amount of a metal catalyst complex comprising a metal and an organic ligand under conditions effective to facilitate an addition reaction and to form a product stream comprising 1,1,1,2,4,4,4-heptachlorobutane, (d) contacting HF with the 1,1,1,2,4,4,4-heptachlorobutane obtained in step (c) in the presence or absence of a fluorination catalyst under conditions effective to facilitate a fluorination reaction and to form a product stream comprising cis- and trans-1,1,1,4,4,4-hexafluoro-2-butene and/or 1,1,1,4,4,4-hexafluoro-2-chlorobutane, (e) optionally dehydrochlorinating the 1,1,1,4,4,4-hexafluoro-2-chlorobutane, in the presence or absence of a dehydrochlorination catalyst under conditions effective to form a product stream comprising a mixture of cis- and trans-1,1,1,4,4,4-hexafluoro-2-butene, and (f) optionally, after isolating the cis-1,1,1,4,4,4-hexafluoro-2-butene product from trans-1,1,1,4,4,4-hexafluoro-2-butene, contacting the trans-1,1,1,4,4,4-hexafluoro-2-butene with an isomerization catalyst under conditions effective to form cis-1,1,1,4,4,4-hexafluoro-2-butene, preferably in substantial amounts.

Optionally but preferably, steps (a), (b) and (c) described above are combined into one reaction, thereby providing another embodiment of the present invention, namely a process comprising the steps of:

(a) contacting carbon tetrachloride with ethylene in the presence of an effective amount of a metal catalyst complex comprising a metal and an organic ligand under conditions effective to facilitate an addition reaction and to form a product stream comprising 1,1,1,2,4,4,4-heptachlorobutane, and (b) contacting HF with the 1,1,1,2,4,4,4-heptachlorobutane formed in step (a) under conditions effective to facilitate a fluorination reaction and to form a product stream mixture comprising 1,1,1,4,4,4-hexafluoro-2-butene and/or 1,1,1,4,4,4-hexafluoro-2-chlorobutane and isolating the 1,1,1,4,4,4-hexafluoro-2-butene therefrom.

DETAILED DESCRIPTION OF THE INVENTION

Starting with carbon tetrachloride and ethylene, 1,1,1,4,4,4-hexafluoro-2-butene (HFO-1336) can be prepared through the following reaction steps:

(a)  $CCl_4 + CH_2=CH_2 \rightarrow CCl_3CH_2CH_2Cl$ (HCC-250)

(b) 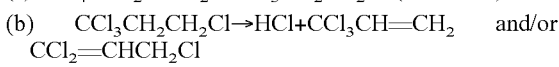 $CCl_3CH_2CH_2Cl \rightarrow HCl + CCl_3CH=CH_2$ and/or $CCl_2=CHCH_2Cl$ (c) 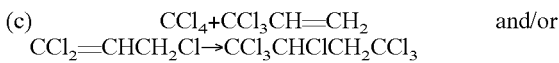 $CCl_4 + CCl_3CH=CH_2$ and/or $CCl_2=CHCH_2Cl \rightarrow CCl_3CHClCH_2CCl_3$ (d) 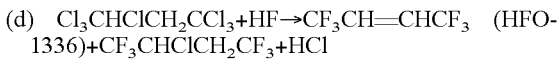 $Cl_3CHClCH_2CCl_3 + HF \rightarrow CF_3CH=CHCF_3$ (HFO-1336) + $CF_3CHClCH_2CF_3 + HCl$ (e) 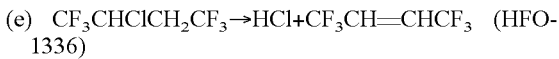 $CF_3CHClCH_2CF_3 \rightarrow HCl + CF_3CH=CHCF_3$ (HFO-1336)

The reactions of steps (a), (b), and (c) may be conducted in one reaction vessel. Two isomers, i.e., cis-$CF_3CH=CHCF_3$ and trans-$CF_3CH=CHCF_3$, are generally produced during the reactions of steps (d) and (e). The cis-isomer is the desired product in some applications. In order to increase the single pass yield of the cis-isomer, the trans-1336 can be isomerized into cis-1336 with the help of an isomerization catalyst, in another optional step (f):

(f) trans-1336→cis-1336

Detailed Process Descriptions

Step (a): 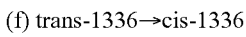 $CCl_4 + CH_2=CH_2 \rightarrow CCl_3CH_2CH_2Cl$ (HCC-250)

In this step, carbon tetrachloride is reacted with ethylene in the presence of an effective amount of a metal catalyst complex comprising a metal and an organic ligand under conditions effective to facilitate an addition reaction and to form a product stream comprising 1,1,1,3-tetrachloropropane.

In preferred embodiment, the metal catalyst complex has a boiling point higher than that of 1,1,1,3-tetrachloropropane product, the metal is a transition metal selected from a group consisting of copper and iron, and the organic ligand is selected from the group consisting of primary and secondary amines having a backbone of 4 or more carbon atoms, nitrites having a backbone of 3 or more carbon atoms, amides having a backbone of two or more carbon atoms, and phosphates or phosphites having a backbone of 3 or more carbon atoms. Particularly, preferred combinations of catalysts and organic ligands are provided in Table 1. Mixtures of the above combination (e.g., mixture of 17 and 18) can also work very well.

TABLE 1

| | Preferred Complexes | |
|---|---|---|
| Combination 1 | Catalyst | Organic Ligand |
| 1 | Cuprous chloride | t-alkylamine |
| 2 | Cuprous chloride | t-butylamine |
| 3 | Cuprous chloride | p-alkylamine |
| 4 | Cuprous chloride | Stearylamine |
| 5 | Cuprous chloride | Laurylamine |
| 6 | Cuprous chloride | Cyclohexylamine |
| 7 | Cuprous chloride | Octylamine |
| 8 | Cuprous chloride | 2-ethylhexylamine |
| 9 | Cuprous chloride | 2-octylamine |
| 10 | Cuprous chloride | Tert-octylamine |
| 11 | Cuprous chloride | Diaminododecane $C_{12}H_{28}N_2$ |
| 12 | Iron powder | Tribuylphosphate |
| 13 | Iron powder | Hexamethylenephosphoramide |
| 14 | Iron powder | Triphenylphosphate |
| 15 | Ferric chloride | Tributylphosphate |
| 16 | Fe powder/Ferric chloride | Triethyl phosphate |
| 17 | Fe powder/Ferric chloride | Trimethyl phosphate |
| 18 | Ferrous chloride | Tributylphosphate |
| 19 | Ferrous chloride | Triphenylphosphate |

The catalyst complex is used in an amount sufficient to catalyze the reaction of carbon tetrachloride and ethylene. Preferably, the concentration of the catalyst in the reaction mixture ranges from about 0.01 to about 10 wt. %, preferably from about 1 to about 5 wt. %, and more preferably from about 1.5 to about 2.5 wt. %.

To achieve favorable selectivity and yields, it is preferable to achieve good mixing of at least a portion of the catalyst complex in the reactions. To this end, the catalyst may be added to the reactor containing carbon tetrachloride, ethylene and organic ligand, or carbon tetrachloride and ethylene may be added to a reactor containing the catalyst and organic ligand.

The reaction should be conducted under operating conditions sufficient to effect the addition reaction of carbon tetrachloride and ethylene in a continuous process. The reaction temperatures can be ranged from about 40° C. to about 180° C., and preferably, from about 50° C. to about 110° C. Reaction pressure is typically maintained by removing a product stream containing the HCC-250 product from the reactor. Generally, the pressure should be maintained to achieve desired contact times. It has been found that reaction pressures of about 1 psig to about 400 psig are preferred, while pressures of about 50 to about 200 psig are even more preferred. Contact times tend to vary according to the catalyst used and the reaction conditions. Suitable results have been obtained with contact times from about 10 seconds to about 10 hours, and preferably from about 1 minute to about 5 hours. Preferably, the reactor effluent is fed to distillation column(s) for organic separation.

Step (b): $CCl_3CH_2CH_2Cl \rightarrow HCl + CCl_3CH=CH_2$
and/or $CCl_2=CHCH_2Cl$

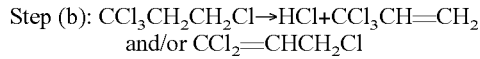

In this step, $CCl_3CH_2CH_2Cl$ is fed to a vapor phase reactor (dehydrochlorination reactor) to be dehydrochlorinated with the help of a dehydrochlorination catalyst to make the desired intermediate $CCl_3CH=CH_2$. The effluent stream exiting reactor may optionally comprise additional components, such as un-reacted $CCl_3CH_2CH_2Cl$, HCl, and $CCl_2=CHCH_2Cl$.

The catalysts may be metal halides, halogenated metal oxides, neutral (or zero oxidation state) metal or metal alloy, or activated carbon in bulk or supported form. In metal halides or metal oxides catalysts, component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Halogenation treatments can include any of those known in the prior art, particularly those that employ HF, $F_2$, HCl, $Cl_2$, HBr, $Br_2$, HI, and $I_2$ as the halogenation source. In neutral, i.e., zero valent, metal and metal alloy catalysts, useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Dehydrochlorination may optionally be carried out in presence or absence of an oxidizing agent. Useful examples of oxidizing agents include, but are not limited to, oxygen and carbon dioxide. Use of an oxidizing agent can extend the life of the catalyst. The oxidizing agent can be pure or diluted with an inert gas such as nitrogen before being introduced into reactor. The level of oxidizing agent is generally from about 1% to about 10% by volume and preferably from about 2% to 5% by volume based on the volume of the organic feed.

The reaction temperatures can be ranged from about 150° C. to about 600° C., preferably from about 200° C. to about 500° C., and even more preferably from about 250° C. to about 400° C. The reaction pressure is preferably about 0 to 150 psig. Preferably, the reactor effluent is fed to a caustic scrubber or to a distillation column to remove the by-product of HCl to produce an acid-free organic product which, optionally, may undergo further purification.

Step (c): $CCl_4 + CCl_3CH=CH_2$ and/or
$CCl_2=CHCH_2Cl \rightarrow CCl_3CHClCH_2CCl_3$

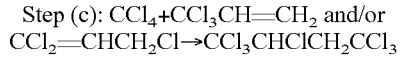

In this step, carbon tetrachloride is reacted with $CCl_3CH=CH_2$ and/or $CCl_2=CHCH_2Cl$ in the presence of an effective amount of a metal catalyst complex comprising a metal and an organic ligand under conditions effective to facilitate an addition reaction and to form a product stream comprising $CCl_3CHClCH_2CCl_3$.

In preferred embodiments, the metal catalyst complex has a boiling point higher than that of $CCl_3CHClCH_2CCl_3$ product, the metal is a transition metal selected from a group consisting of copper and iron, and the organic ligand is selected from the group consisting of primary and secondary amines having a backbone of 4 or more carbon atoms, nitrites having a backbone of 3 or more carbon atoms, amides having a backbone of two or more carbon atoms, and phosphates or phosphites having a backbone of 3 or more carbon atoms. Particularly, preferred combinations of catalysts and organic ligands are provided in Table 2. Mixtures of the above combination (e.g., mixture of 17 and 18) can also work very well.

TABLE 2

| | Preferred Complexes | |
|---|---|---|
| Combination 1 | Catalyst | Organic Ligand |
| 1 | Cuprous chloride | t-alkylamine |
| 2 | Cuprous chloride | t-butylamine |
| 3 | Cuprous chloride | p-alkylamine |
| 4 | Cuprous chloride | Stearylamine |
| 5 | Cuprous chloride | Laurylamine |
| 6 | Cuprous chloride | Cyclohexylamine |
| 7 | Cuprous chloride | Octylamine |
| 8 | Cuprous chloride | 2-ethylhexylamine |

TABLE 2-continued

| | Preferred Complexes | |
|---|---|---|
| Combination 1 | Catalyst | Organic Ligand |
| 9 | Cuprous chloride | 2-octylamine |
| 10 | Cuprous chloride | Tert-octylamine |
| 11 | Cuprous chloride | Diaminododecane $C_{12}H_{28}N_2$ |
| 12 | Iron powder | Tribuylphosphate |
| 13 | Iron powder | Hexamethylenephosphoramide |
| 14 | Iron powder | Triphenylphosphate |
| 15 | Ferric chloride | Tributylphosphate |
| 16 | Fe powder/Ferric chloride | Triethyl phosphate |
| 17 | Fe powder/Ferric chloride | Trimethyl phosphate |
| 18 | Ferrous chloride | Tributylphosphate |
| 19 | Ferrous chloride | Triphenylphosphate |

The catalyst complex is used in an amount sufficient to catalyze the reaction of carbon tetrachloride and $CCl_3CH=CH_2$ and/or $CCl_2=CHCH_2Cl$. Preferably, the concentration of the catalyst in the reaction mixture ranges from about 0.01 to about 10 wt. %, preferably from about 1 to about 5 wt. %, and more preferably from about 1.5 to about 2.5 wt. %.

To achieve favorable selectivity and yields, it is preferable to achieve good mixing of at least a portion of the catalyst complex in the reactions. To this end, the catalyst may be added to the reactor containing carbon tetrachloride, $CCl_3CH=CH_2$ and/or $CCl_2=CHCH_2Cl$ and organic ligand, or carbon tetrachloride and $CCl_3CH=CH_2$ and/or $CCl_2=CHCH_2Cl$ may be added to a reactor containing the catalyst and organic ligand.

The reaction should be conducted under operating conditions sufficient to effect the addition reaction of carbon tetrachloride and $CCl_3CH=CH_2$ and/or $CCl_2=CHCH_2Cl$ in a continuous process. The reaction temperatures can be ranged from about 40° C. to about 180° C., and preferably, from about 50° C. to about 110° C. Reaction pressure is typically maintained by removing a product stream containing $CCl_3CHClCH_2CCl_3$ product from the reactor. Generally, the pressure should be maintained to achieve desired contact times. It has been found that reaction pressures of about 1 psig to about 400 psig are preferred, while pressures of about 50 psig to about 200 psig are even more preferred. Contact times tend to vary according to the catalyst used and the reaction conditions. Suitable results have been obtained with contact times from about 10 seconds to about 10 hours, and preferably from about 1 minute to about 5 hours. Preferably, the reactor effluent is fed to distillation column(s) for organic separation.

Optionally, but preferably, steps (a), (b) and (c) are combined in one reaction step (a)', in which $CCl_3CHClCH_2CCl_3$ is directly synthesized from carbon tetrachloride and ethylene.

Step (a)': $CCl_4 + CH_2 \rightarrow CH_2 \rightarrow CCl_3CHClCH_2CCl_3$

In this step, carbon tetrachloride is reacted with ethylene in the presence of an effective amount of a metal catalyst complex comprising a metal and an organic ligand under conditions effective to facilitate an addition reaction and to form a product stream comprising $CCl_3CHClCH_2CCl_3$.

In a preferred embodiment, the metal catalyst complex has a boiling point higher than that of $CCl_3CHClCH_2CCl_3$ product, the metal is a transition metal selected from a group consisting of copper and iron, and the organic ligand is selected from the group consisting of primary and secondary amines having a backbone of 4 or more carbon atoms, nitrites having a backbone of 3 or more carbon atoms, amides having a backbone of two or more carbon atoms, and phosphates or phosphites having a backbone of 3 or more carbon atoms. Particularly, preferred combinations of catalysts and organic ligands are provided in Table 3. Mixtures of the Table 2 complexes (e.g., a mixture of 17 and 18) can also work very well.

TABLE 3

| | Preferred Complexes | |
|---|---|---|
| Combination 1 | Catalyst | Organic Ligand |
| 1 | Cuprous chloride | t-alkylamine |
| 2 | Cuprous chloride | t-butylamine |
| 3 | Cuprous chloride | p-alkylamine |
| 4 | Cuprous chloride | Stearylamine |
| 5 | Cuprous chloride | Laurylamine |
| 6 | Cuprous chloride | Cyclohexylamine |
| 7 | Cuprous chloride | Octylamine |
| 8 | Cuprous chloride | 2-ethylhexylamine |
| 9 | Cuprous chloride | 2-octylamine |
| 10 | Cuprous chloride | Tert-octylamine |
| 11 | Cuprous chloride | Diaminododecane $C_{12}H_{28}N_2$ |
| 12 | Iron powder | Tribuylphosphate |
| 13 | Iron powder | Hexamethylenephosphoramide |
| 14 | Iron powder | Triphenylphosphate |
| 15 | Ferric chloride | Tributylphosphate |
| 16 | Fe powder/Ferric chloride | Triethyl phosphate |
| 17 | Fe powder/Ferric chloride | Trimethyl phosphate |
| 18 | Ferrous chloride | Tributylphosphate |
| 19 | Ferrous chloride | Triphenylphosphate |

The catalyst complex is used in an amount sufficient to catalyze the reaction of carbon tetrachloride and ethylene. Preferably, the concentration of the catalyst in the reaction mixture ranges from about 0.01 to about 10 wt. %, preferably from about 1 to about 5 wt. %, and more preferably from about 1.5 to about 2.5 wt. %.

To achieve favorable selectivity and yields, it is preferable to achieve good mixing of at least a portion of the catalyst complex in the reactions. To this end, the catalyst may be added to the reactor containing carbon tetrachloride, ethylene and organic ligand, or carbon tetrachloride and ethylene may be added to a reactor containing the catalyst and organic ligand.

The reaction should be conducted under operating conditions sufficient to effect the addition reaction of carbon tetrachloride and ethylene in a continuous process. The reaction temperatures can be ranged from about 40° C. to about 180° C., and preferably, from about 50° C. to about 110° C. Reaction pressure is typically maintained by removing a product stream containing the $CCl_3CHClCH_2CCl_3$ product from the reactor. Generally, the pressure should be maintained to achieve desired contact times. It has been found that reaction pressures of about 1 psig to about 400 psig are preferred, while pressures of about 50 to about 200 psig are even more preferred. Contact times tend to vary according to the catalyst used and the reaction conditions. Suitable results have been obtained with contact times from about 10 seconds to about 10 hours, and preferably from about 1 minute to about 5 hours. Preferably, the reactor effluent is fed to distillation column(s) for organic separation.

Step (d): CCl$_3$CHClCH$_2$CCl$_3$+
HF→CF$_3$CH=CHCF$_3$(HFO-1336)+
CF$_3$CHClCH$_2$CF$_3$+HCl In this step, HF is reacted with 1,1,1,2,4,4,4-heptachlorobutane formed in step (d) in the presence of a fluorination catalyst under conditions effective to facilitate a fluorination reaction and to form a product stream comprising 1,1,1,4,4,4-hexafluoro-2-butene and/or 1,1,1,4,4,4-hexafluoro-2-chlorobutane. The effluent stream exiting reactor may optionally comprise additional components, such as un-reacted HF, and CF$_3$CHClCH$_2$CF$_3$. The fluorination process may be carried out in a vapor phase or a liquid phase.

In vapor-phase fluorination, HF (hydrogen fluoride gas) is fed continuously through the catalyst bed. After a short time with only the HF feed stream, CCl$_3$CHClCH$_2$CCl$_3$ is fed continuously through the catalyst bed at a ratio of about 1:6 to about 1:30 and preferably from about 1:10 to about 1:20 CCl$_3$CHClCH$_2$CCl$_3$/HF mole ratio. The reaction between HF and CCl$_3$CHClCH$_2$CCl$_3$ is carried out at a temperature from about 100° C. to about 500° C., preferably from about 200° C. to about 350° C.; and at a pressure of about 5 psig to about 200 psig (pounds per square inch gauge), preferably from about 20 psig to about 100 psig. Suitable vapor phase solid catalysts include, but are not limited to chromium, aluminum, cobalt, manganese, nickel and iron oxides, hydroxides, halides, oxyhalides, inorganic salts thereof and their mixtures.

Chromium (III) oxides such as crystalline chromium oxide or amorphous chromium oxide are preferred with amorphous chromium oxide being most preferred. Chromium oxide (Cr$_2$O$_3$) is a commercially available material which may be purchased in a variety of particle sizes. The catalyst may be supported on a substrate, such as on activated carbon, or may be unsupported or free-standing. In addition to activated carbon, useful catalyst supports include: alumina, fluorinated alumina, aluminum fluoride, alkaline earth metal oxides, fluorinated alkaline earth metal oxides, zinc oxide, zinc fluoride, tin oxide, and tin fluoride. Optionally but preferably, metal oxide catalysts are subject to fluorination treatment in HF flow at sufficiently high temperatures prior to reaction.

In liquid phase fluorination, a liquid phase fluorination catalyst is charged in a liquid form to a reactor and optionally activated with HF. Non-exhaustive list includes Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof.

Specific non-exclusive examples of liquid phase fluorination catalysts are SbCl$_5$, SbCl$_3$, SbF$_5$, SnCl$_4$, TaCl$_5$, TiCl$_4$, NbCl$_5$, MoCl$_6$, FeCl$_3$, a fluorinated species of SbCl$_5$, a fluorinated species of SbCl$_3$, a fluorinated species of SnCl$_4$, a fluorinated species of TaCl$_5$, a fluorinated species of TiCl$_4$, a fluorinated species of NbCl$_5$, a fluorinated species of MoCl$_6$, a fluorinated species of FeCl$_3$, or combinations thereof. Antimony pentachloride is most preferred.

The activated catalyst is then heated to the desired reaction temperature of about 30° C. to about 200° C., preferably from about 50° C. to about 120° C.; and the pressure is kept between about 15 psig to about 200 psig, preferably from about 50 psig to about 175 psig. After a short time with only HF feed, a CCl$_3$CHClCH$_2$CCl$_3$ feed stream is fed continuously through the catalyst at a ratio of about 1:6 to about 1:30 and preferably about 1:10 to about 1:20 CCl$_3$CHClCH$_2$CCl$_3$/HF mole ratio. If necessary, the catalyst can be kept activated by the continuous or batch addition of Cl$_2$ or a similar oxidizing agent.

The fluorination reaction is preferably carried out to achieve a conversion of about 70% or more, preferably about 90% or more, and most preferably about 93% or more. The selectivity for CF$_3$CH=CHCF$_3$ attained is preferably about 60% or more and most preferably about 80% or more.

The fluorination is preferably carried out in a corrosion-resistant reaction vessel. Examples of corrosion-resistant materials are Hastelloy, Nickel, Incoloy, Inconel, Monel and fluoropolymer linings. The vessel may have a fixed catalyst bed, or contain liquid catalyst. If desired, inert gases such as nitrogen or argon may be employed in the reactor during operation. Preferably, the reactor effluent is fed to a caustic scrubber or to a distillation column or to an extractor to remove the by-product of HCl and un-converted HF to produce an acid-free organic product which, optionally, may undergo further purification.

Step (e): CF$_3$CHClCH$_2$CF$_3$→HCl+CF$_3$CH=CHCF$_3$
(HFO-1336)

In this step, CF$_3$CHClCH$_2$CF$_3$, formed in step (d) as by-product, is fed to a vapor phase reactor (which contains a dehydrochlorination catalyst) to be dehydrochlorinated to make the desired product HFO-1336.

The catalysts may be metal halides, halogenated metal oxides, neutral (or zero oxidation state) metal or metal alloy, or activated carbon in bulk or supported form. In metal halides or metal oxides catalysts, component metals include, but are not limited to, Cr$^{3+}$, Fe$^{3+}$, Mg$^{2+}$, Ca$^{2+}$, Ni$^{2+}$, Pd$^{2+}$, Li$^+$, Na$^+$, K$^+$, and Cs$^+$. Component halogens include, but are not limited to, F$^-$, Br$^-$, and I$^-$. Halogenation treatments can include any of those known in the prior art, particularly those that employ HF, F$_2$, HCl, Cl$_2$, HBr, Br$_2$, HI, and I$_2$ as the halogenation source.

In neutral, i.e., zero valent, metals and metal alloys catalysts, useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625.

Dehydrochlorination may optionally be carried out in presence or absence of an oxidizing agent. Useful examples of oxidizing agents include, but are not limited to, oxygen and carbon dioxide. Use of an oxidizing agent can extend the life of the catalyst. The oxidizing agent can be pure or diluted with an inert gas such as nitrogen before being introduced into reactor. The level of oxidizing agent is generally from about 1% to about 10% by volume and preferably from about 2% to 5% by volume based on the volume of the organic feed.

The reaction temperatures can be ranged from about 150° C. to about 600° C., preferably from about 200° C. to about 500° C., and even more preferably from about 250° C. to about 400° C. The reaction pressure is preferably from about 0 psig to 150 psig. Preferably, the reactor effluent is fed to a caustic scrubber or to a distillation column to remove the by-product of HCl to produce an acid-free organic product which, optionally, may undergo further purification.

Step (f): trans-1336 cis-1336

Two isomers, i.e., cis-CF$_3$CH=CHCF$_3$ and trans-CF$_3$CH=CHCF$_3$, are generally produced during reactions of steps (d) and (e). When the cis-isomer is the desired product, to increase the single pass yield of the cis-isomer, the trans-1336 is optionally but preferably isomerized into cis-1336 in a vapor phase reactor containing an isomerization catalyst. If the trans-isomer is preferred, similar isomerization reaction can be used to enrich the product stream with more trans-1336.

Three kinds of catalysts, namely, halogenated metal oxides, Lewis acid metal halides, and zero-valent metals, can be used as isomerization catalysts. For catalysts which are halogenated metal oxide catalysts (which are sometimes referred to herein for convenience as HMO catalysts) and Lewis Acid catalysts (which are sometimes referred to herein for convenience as LA catalysts), it is generally preferred that the catalysts include a transition metal or Al, and preferably when a transition metal is present it is selected from the group consisting of transition metals with an atomic number from about 21 to about 57, and combinations of these.

From among the transition metals for use in HMO and LA catalysts, metals from Group VIB are preferred in certain embodiments, with Cr being especially preferred from among this group. In general for HMO and LA catalysts which include a transition metal component, the metal is preferably selected from the group consisting of Cr, Mo, V, Nb, Fe, La, Ni, Zn and combinations of these. In general for HMO and LA catalysts which include rare earth metal component, the metal is preferably Ce. In general for HMO and LA catalysts which include boron metal component, the metal is preferably selected from Al, Tl, and combinations of these. In general for HMO and LA catalysts which include an alkali earth metal component, the metal is preferably Mg. In general for HMO and LA catalysts which include alkali metal components, the metal is preferably selected from Li, Na, K and combinations of these. With respect to neutral metals catalysts (which are sometimes referred to herein for convenience as NM catalysts), it is generally preferred that the catalysts include one or more transition metals selected from groups VII and IB, with Co and Pd being preferred in certain embodiments.

In preferred embodiments, reaction temperatures may be ranged from about 50° C. to about 600° C., preferably from about 100° C. to about 400° C., and even more preferably from about 150° C. to about 300° C. It is also contemplated that a wide variety of pressures may be used in connection with the processes of the present invention. Nevertheless, in certain preferred embodiments, the reaction is carried out under pressure conditions ranging from a vacuum of about 5 ton to about 200 psig. It is also contemplated that a wide variety of contact times for the preferred reactions of the present invention may be used. Nevertheless, in certain preferred embodiments, the residence time is preferably from about 0.5 seconds to about 600 seconds.

One aspect of preferred embodiments of the present invention includes converting the trans-1336 to the cis-form, preferably at a conversion of at least about 1 percent, more preferably at least around 20%, and even more preferably at least about 50%, while at the same time preferably achieving a selectivity to the cis-form of the compound that is at least about 80%, even more preferably at least about 95%, and in certain highly preferred embodiments at least about 98%.

The following examples are given as specific illustrations of the invention. It should be noted, however, that the invention is not limited to the specific details set forth in the examples.

EXAMPLE 1

Production of $CCl_3CH_2CH_2Cl$ (HCC-250) from Carbon Tetrachloride and Ethylene To a 0.5 inch by 40 inch plug flow reactor that is packed iron wires, a mixture (50/50 mole %) of ethylene and carbon tetrachloride is fed at about 1.5 g/min. A catalyst mixture of ferric chloride, tributylphosphate and carbon tetrachloride, which is prepared in a catalyst pre-mix tank (2 liter), is also fed to the reactor simultaneously at about 2 g/min. The reactor is operated at 80° C. to 100° C. and controlled at about 30 psig to 100 psig. The effluent of the plug flow reactor is fed to a distillation column, which is operated under vacuum, for example at 30 mmHg, and about 50° C. to 60° C. The unreacted carbon tetrachloride with trace amounts of ethylene are distilled off from this distillation column, condensed and fed to the catalyst pre-mix tank. The bottom mixture from this distillation is fed to a second distillation that is operated under vacuum, at about 50 mmHg and 80° C. to 90° C. The crude HCC-250 product is collected from the top of the column. The bottom mixture that contains the catalyst mixture, ferric chloride, ferrous chloride and tributylphosphate is fed back to the catalyst pre-mix tank and subsequently, recycled back to the reactor. The crude HCC-250 contains 1.4 grams of HCC-250. The yield is greater than 90%.

EXAMPLE 2

Production of $CCl_3CH\!=\!CH_2$

A cylindrical ¾ inch ID Monel reactor immersed into a 3-zone electrical furnace is used in the dehydrochlorination reaction of HCC-250. Process temperatures are recorded using a 5-point thermocouple placed inside the reactor and through the catalyst bed. 20 cc of 5% $FeCl_3$/carbon catalyst is charged into the reactor. HCC-250 is fed into the bottom of the vertically mounted reactor at a rate of 12 g/h and is vaporized before reaching catalyst bed. The reaction is conducted at 350° C. and 1 atm. Effluent gases are passed through a gas sampling tube so that the progress of the reaction is monitored periodically via GC analysis of the contents of the gas sampling tube. Analysis indicates the effluent gases contain about 92% $CCl_3CH\!=\!CH_2$, about 3% $CCl_2\!=\!CHCH_2Cl$ and about 5% HCC-250.

EXAMPLE 3

Production of $CCl_3CHClCH_2CCl_3$

To a 1 liter glass-lined autoclave equipped with an agitator, a mixture (50/50 mole %) of $CCl_3CH\!=\!CH_2$ and carbon tetrachloride is fed at about 1.5 g/min. A catalyst mixture of ferric chloride, tributyl phosphate and carbon tetrachloride, which is prepared in a catalyst pre-mix tank (2 liters), is also fed to the reactor simultaneously at about 2 g/min. The reactor is operated at about 100° C. and controlled at less than 80 psig. The product mixture is removed continuously by using a dip tube, which is inserted about ⅔ of the autoclave. The product mixture is fed to a distillation column, which is operated at atmospheric pressure and about 80° C. The unreacted carbon tetrachloride with trace amounts of $CCl_3CH\!=\!CH_2$ are distilled off from this distillation column and fed to the catalyst pre-mix tank. The bottom mixture from this distillation is fed to a second distillation that is operated under vacuum, at about 50 mmHg and 80° C. to 90° C. The crude $CCl_3CHClCH_2CCl_3$ product is collected from the top of the column. The bottom mixture that contains the catalyst mixture, ferric chloride and tributyl phosphate is fed back to the catalyst pre-mix tank. The crude $CCl_3CHClCH_2CCl_3$ contains 1.35 grams of $CCl_3CHClCH_2CCl_3$. The yield is greater than 90%.

EXAMPLE 4

Production of $CCl_3CHClCH_2CCl_3$ Directly from Carbon Tetrachloride and Ethylene To a 1 liter glass-lined autoclave equipped with an agitator, a mixture (50/50 mole %) of ethylene and carbon tetrachloride is fed at about 1.5 g/min. A catalyst mixture of Fe powder, ferric chloride, tributylphosphate and carbon tetrachloride, which is prepared in a catalyst pre-mix tank (2 liters), is also fed to the reactor simultaneously at about 2 g/min. The reactor is operated at about 100° C. and controlled at less than 80 psig. The product mixture is removed continuously by using a dip tube, which is inserted about ⅔ of the autoclave. The product mixture is fed to a distillation column, which is operated at atmospheric pressure and about 80° C. The unreacted carbon tetrachloride with trace amounts of ethylene are distilled off from this distillation column and fed to the catalyst pre-mix tank. The bottom mixture from this distillation is fed to a second distillation that is operated under vacuum, at about 50 mmHg and 80° C. to 90° C. The crude $CCl_3CHClCH_2CCl_3$ product is collected from the top of the column. The bottom mixture that contains the catalyst mixture, Fe powder, ferric chloride and tributyl phosphate is fed back to the catalyst pre-mix tank. The crude $CCl_3CHClCH_2CCl_3$ contains 1.35 grams of $CCl_3CHClCH_2CCl_3$. The yield is greater than 90%.

EXAMPLE 5

Production of $CF_3CH=CHCF_3$ (HFO-1336) and $CF_3CHClCH_2CF_3$

The vapor phase fluorination of $CCl_3CHClCH_2CCl_3$ is conducted in the presence fluorinated $Cr_2O_3$ catalyst. A continuous vapor phase fluorination reaction system consisting of $N_2$, HF, and organic feed systems, feed vaporizer, superheater, 4 inch ID (inside diameter) Monel reactor, acid scrubber, drier, and product collection system is used to study the reaction. The reactor is loaded with about 6.5 liters of fluorinated $Cr_2O_3$ catalyst. The reactor is then heated to a reaction temperature of about 240° C. with a $N_2$ purge flowing over the catalyst. The reactor is at about 3 psig of pressure. HF feed is then introduced to the reactor via the vaporizer and superheater as a co-feed with the $N_2$ for 15 minutes when the $N_2$ flow is stopped. The HF flow rate is adjusted to 1.4 lb/hr and then $CCl_3CHClCH_2CCl_3$ feed is started to the reactor via the vaporizer and superheater. The feed rate of $CCl_3CHClCH_2CCl_3$ is kept steady at about 1.2 lb/hr and HF feed is kept steady at 1.4 lb/hr for about an 18 to 1 mole ratio of HF to $CCl_3CHClCH_2CCl_3$. Once the reaction starts the catalyst bed temperature rises to a range of 250° C. to 260° C. The concentrations of $CF_3CH=CHCF_3$, $CF_3CHClCH_2CF_3$, and $CCl_3CHClCH_2CCl_3$ in the effluent of the reactor are 92.9, 4.9, and 1.1 GC Area %, respectively.

EXAMPLE 6

Production of $CF_3CH=CHCF_3$ (HFO-1336) from $CF_3CHClCH_2CF_3$

A cylindrical ¾ inch ID Monel reactor immersed into a 3-zone electrical furnace is used in the dehydrochlorination reaction of $CF_3CHClCH_2CF_3$. Process temperatures are recorded using a 5-point thermocouple placed inside the reactor and through the catalyst bed. 20 cc of fluorinated chromia catalyst is charged into the reactor. $CF_3CHClCH_2CF_3$ is fed into the bottom of the vertically mounted reactor at a rate of 12 g/h and is vaporized before reaching catalyst bed. The reaction is conducted at 350° C. and 1 atm. Effluent gases are passed through a gas sampling tube so that the progress of the reaction is monitored periodically via GC analysis of the contents of the gas sampling tube. Analysis indicates the effluent gases contain about 91% $CF_3CH=CHCF_3$, and about 8% $CF_3CHClCH_2CF_3$.

EXAMPLE 7

Production of $CF_3CH=CHCF_3$ (HFO-1336) from $CCl_3CHClCH_2CCl_3$

The liquid phase fluorination of $CCl_3CHClCH_2CCl_3$ is conducted in the presence $SbCl_5$. About 6100 grams of $SbCl_5$ are contained in a Teflon®-lined liquid phase reactor (Teflon is a trademark of E.I. duPont de Nemours & Co) equipped with a 2-inch ID packed column and a condenser. The reactor is 2.75-inch ID×36-inch long. A large excess of $Cl_2$ is first added to the reactor to ensure that the catalyst is in a pentavalent state. The reactor is heated to about 85° C. to 87° C. HF feed is started first. When 1.3 lbs (pounds) of HF have been added the $CCl_3CHClCH_2CCl_3$ feed is started. The purity of the $CCl_3CHClCH_2CCl_3$ feed stock is about 99 GC area % (gas chromatograph). The experiment runs continuously for 71 hours. During this run, chlorine is fed batchwise about every 4 hours throughout the run to keep the catalyst active. The feeds averaged 0.495 lbs/hr HF, and 0.411 lbs/hr $CCl_3CHClCH_2CCl_3$ for an 18/1 ratio of HF/$CCl_3CHClCH_2CCl_3$, and 135 seconds residence time. The reactor temperature range for the experiment is 78° C. to 91° C. and the pressure range is 85 psig to 115 psig (pounds per square inch gauge). The organic crude material collected from the run is run on a gas chromatograph. The concentrations of $CF_3CH=CHCF_3$, and $CCl_3CHClCH_2CCl_3$ in organic phase are 97.9, and 1.0 GC Area %, respectively.

EXAMPLE 8

Production of Cis-$CF_3CH=CHCF_3$ from Trans-$CF_3CH=CHCF_3$

A cylindrical Monel reactor of ¾ inch ID immersed into a 3-zone electrical furnace is used in the isomerization reaction of trans-$CF_3CH=CHCF_3$. Process temperatures are recorded using a 5-point thermocouple placed inside the reactor and through the catalyst bed. 20 cc of fluorinated chromia catalyst is charged into the reactor. Trans-$CF_3CH=CHCF_3$ is fed into the bottom of the vertically mounted reactor at a rate of 12 g/h and is vaporized before reaching catalyst bed. The reaction is conducted at 250° C. and 1 atm. Effluent gases are passed through a gas sampling tube so that the progress of the reaction is monitored periodically via GC analysis of the contents of the gas sampling tube. Analysis indicates the effluent gases contain about 61% cis-$CF_3CH=CHCF_3$, and about 38% trans-$CF_3CH=CHCF_3$.

While the present invention has been particularly shown and described with reference to preferred embodiments, it will be readily appreciated by those of ordinary skill in the art that various changes and modifications may be made without departing from the spirit and scope of the invention. It is intended that the claims be interpreted to cover the disclosed embodiment, those alternatives which have been discussed above and all equivalents thereto.

What is claimed is:

1. A process for the manufacture of 1,1,1,4,4,4-hexafluoro-2-butene comprising the steps of:
   (a) contacting carbon tetrachloride with ethylene in the presence of an effective amount of a metal catalyst complex comprising a metal and an organic ligand under conditions effective to facilitate an addition reaction and to form a product stream comprising 1,1,1,2,4,4,4-heptachlorobutane, and
   (b) contacting HF with the 1,1,1,2,4,4,4-heptachlorobutane formed in step (a) under conditions effective to facilitate a fluorination reaction and to form a product stream mixture comprising 1,1,1,4,4,4-hexafluoro-2-butene and/or 1,1,1,4,4,4-hexafluoro-2-chlorobutane and isolating the 1,1,1,4,4,4-hexafluoro-2-butene therefrom.

2. The process of claim 1, wherein the metal catalyst complex in step (a) has a boiling point higher than that of 1,1,1,2,4,4,4-heptachlorobutane.

3. A process for the manufacture of 1,1,1,4,4,4-hexafluoro-2-butene comprising the steps of:
   (a) contacting carbon tetrachloride with ethylene in the presence of an effective amount of a metal catalyst complex comprising a metal and an organic ligand under conditions effective to facilitate an addition reaction and to form a first product stream comprising 1,1,1,3-tetrachloropropane,
   (b) dehydrochlorinating the 1,1,1,3-tetrachloropropane formed in step (a) under conditions effective to form a second product stream mixture comprising 3,3,3-trichloro-1-propene and/or 1,1,3-trichloro-1-propene,
   (c) contacting carbon tetrachloride with the product stream mixture formed in step (b) in the presence of an effective amount of a metal catalyst complex comprising a metal and an organic ligand under conditions effective to facilitate an addition reaction and to form a third product stream comprising 1,1,1,2,4,4,4-heptachlorobutane, and
   (d) contacting HF with the 1,1,1,2,4,4,4-heptachlorobutane formed in step (c) under conditions effective to facilitate a fluorination reaction and to form a fourth product stream mixture comprising 1,1,1,4,4,4-hexafluoro-2-butene and/or 1,1,1,4,4,4-hexafluoro-2-chlorobutane and isolating the 1,1,1,4,4,4-hexafluoro-2-butene therefrom.

4. The process of claim 3, wherein the metal catalyst complex in step (a) has a boiling point higher than that of 1,1,1,3-tetrachloropropane.

5. The process of claim 2 or 4, wherein the metal in the metal catalyst complex is a transition metal or a mixture of transition metals.

6. The process of claim 5, wherein the transition metal is selected from the group consisting of copper, iron and mixtures thereof.

7. The process of claim 5, wherein the organic ligand in the metal catalyst complex is selected from the group consisting of primary and secondary amines having a backbone of 4 or more carbon atoms, nitrites having a backbone of 3 or more carbon atoms, amides having a backbone of two or more carbon atoms, and phosphates or phosphites having a backbone of 3 or more carbon atoms.

8. The process of claim 3, wherein step (b) takes place in the absence of a dehydrochlorination catalyst.

9. The process of claim 3, wherein step (b) takes place in the presence of a dehydrochlorination catalyst.

10. The process of claim 9, wherein the dehydrochlorination catalyst is selected from the group consisting of metal halides, halogenated metal oxides, neutral metal and metal alloys, activated carbon in bulk and supported form, and mixtures thereof.

11. The process of claim 10, wherein the metals in the metal halide and metal oxide catalysts are selected from the group consisting of $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, $Cs^+$, and mixtures thereof.

12. The process of claim 9, wherein the metals in the neutral metal and metal alloy catalysts are selected from the group consisting of Pd, Pt, Rh, Fe, Co, Ni, Cu, Mo, Cr, Mn, alloys and mixtures thereof.

13. The process of claim 3, wherein the metal catalyst complex in step (c) has a boiling point higher than that of 1,1,1,2,4,4,4-heptachlorobutane.

14. The process of claim 13, wherein the metal in the metal catalyst complex is a transition metal or a mixture of transition metals.

15. The process of claim 14, wherein the transition metal is selected from the group consisting of copper, iron and mixtures thereof.

16. The process of claim 13, wherein the organic ligand in the metal catalyst complex is selected from the group consisting of primary and secondary amines having a backbone of 4 or more carbon atoms, nitrites having a backbone of 3 or more carbon atoms, amides having a backbone of two or more carbon atoms, and phosphates or phosphites having a backbone of 3 or more carbon atoms.

17. The process of claim 1 or 3, wherein the fluorination reaction takes place in the absence of a fluorination catalyst.

18. The process of claim 1 or 3, wherein the fluorination reaction takes place in the presence of a fluorination catalyst.

19. The process of claim 18, wherein the fluorination reaction takes place in a vapor phase.

20. The process of claim 19, wherein the vapor phase solid catalyst is selected from the group consisting of chromium, aluminum, cobalt, manganese, nickel and iron oxides, hydroxides, halides, oxyhalides, inorganic salts thereof and mixtures thereof.

21. The process of claim 20, wherein the vapor phase solid catalyst is a chromium (III) oxide.

22. The process of claim 21, wherein the chromium (III) oxide is a crystalline chromium oxide.

23. The process of claim 21, wherein the chromium (III) oxide is an amorphous chromium oxide.

24. The process of claim 18, wherein the fluorination reaction takes place in a liquid phase.

25. The process of claim 24, wherein the liquid phase fluorination catalyst is selected from the group consisting of $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, and mixtures thereof.

26. The process of claim 25, wherein the liquid phase fluorination catalyst is antimony pentachloride.

27. The process of claim 3, further comprising step (e), dehydrochlorinating the 1,1,1,4,4,4-hexafluoro-2-chlorobutane under conditions effective to form a product stream comprising 1,1,1,4,4,4-hexafluoro-2-butene.

28. The process of claim 27, wherein step (e) takes place in the presence of a dehydrochlorination catalyst.

29. The process of claim 28, wherein the dehydrochlorination catalyst is selected from the group consisting of metal halides, halogenated metal oxides, neutral metal and metal alloys, activated carbon in bulk and supported form, and mixtures thereof.

30. The process of claim 29, wherein the metals in the metal halide and metal oxide catalysts are selected from the group consisting of $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, $Cs^+$, and mixtures thereof.

31. The process of claim 29, wherein the metals in the neutral metal and metal alloy catalysts are selected from the group consisting of Pd, Pt, Rh, Fe, Co, Ni, Cu, Mo, Cr, Mn, alloys and mixtures thereof.

32. The process of claim 27, wherein step (e) takes place in the presence of an oxidizing agent.

33. The process of claim 32, wherein the oxidizing agent is selected from the group consisting of oxygen, carbon dioxide, and mixtures thereof.

34. The process of claim 32, wherein the oxidizing agent is further diluted with an inert gas.

35. The process of claim 27, wherein step (e) takes place in the absence of an oxidizing agent.

36. The process of claim 27, wherein step (e) takes place in the absence of a dehydrochlorination catalyst.

37. The process of claim 1 or 3, further comprising the step of contacting trans-1,1,1,4,4,4-hexafluoro-2-butene with an isomerization catalyst under conditions effective to form cis-1,1,1,4,4,4-hexafluoro-2-butene.

38. The process of claim 37, wherein the isomerization catalyst is selected from the group consisting of halogenated metal oxides, Lewis acid metal halides, zero-valent metals, and mixtures thereof.

39. The process of claim 38, wherein the halogenated metal oxide catalyst or the Lewis Acid metal halide catalyst further includes a boron metal component.

40. The process of claim 39, wherein the catalyst metal is selected from the group consisting of Al, Tl, and mixtures thereof.

41. The process of claim 38, wherein the halogenated metal oxide catalysts and Lewis Acid catalysts include a transition metal or Al.

42. The process of claim 41, wherein the transition metal is selected from the group consisting of Cr, Mo, V, Nb, Fe, La, Ni, Zn and mixtures thereof.

43. The process of claim 42, wherein the transition metal is Cr.

44. The process of claim 38, wherein the neutral metal catalyst is selected from the group consisting of the transition metals in Groups VII and IB, and mixtures thereof.

* * * * *